United States Patent
Del Rio et al.

(10) Patent No.: US 6,746,153 B2
(45) Date of Patent: Jun. 8, 2004

(54) BEARINGS FOR SURGICAL INSTRUMENTS

(75) Inventors: Eddy Del Rio, Royal Palm Beach, FL (US); Jose M. Lamanna, Jupiter, FL (US); Douglas A. Perry, Palm Beach Gardens, FL (US); Thomas E. Anspach, Jupiter, FL (US)

(73) Assignee: The Anspach Effort, Inc., Palm Beach Gardens, FL (US)

( * ) Notice: Subject to any disclaimer, the term of this patent is extended or adjusted under 35 U.S.C. 154(b) by 124 days.

(21) Appl. No.: 09/962,989

(22) Filed: Sep. 25, 2001

(65) Prior Publication Data

US 2003/0063823 A1 Apr. 3, 2003

(51) Int. Cl.[7] ................................. F16C 9/02
(52) U.S. Cl. ....................... 384/276; 384/441
(58) Field of Search ..................... 384/129, 100, 384/416, 418, 419, 440, 441, 276, 280, 282

(56) References Cited

U.S. PATENT DOCUMENTS

| | | | | |
|---|---|---|---|---|
| 4,424,045 A | * | 1/1984 | Kulischenko et al. | 464/52 |
| 5,046,377 A | * | 9/1991 | Wilkes et al. | 74/431 |
| 5,127,745 A | * | 7/1992 | Momose et al. | 384/276 |
| 5,494,359 A | * | 2/1996 | Del Rio et al. | 384/518 |
| 5,601,560 A | * | 2/1997 | Del Rio et al. | 608/80 |
| 5,823,774 A | * | 10/1998 | Abbott et al. | 384/478 |
| 5,988,889 A | * | 11/1999 | Barnhart et al. | 384/441 |
| 6,015,236 A | * | 1/2000 | Niegel et al. | 384/276 |
| 6,316,534 B1 | * | 11/2001 | Shimokusuzono et al. | 524/284 |

OTHER PUBLICATIONS

DuPont Vesel "Innovative Vespel–Elastomer Bearing Solutions for Electrical Motors".*

* cited by examiner

*Primary Examiner*—Matthew C. Graham
(74) *Attorney, Agent, or Firm*—Norman Friedland

(57) ABSTRACT

A journal bearing for a high speed surgical drill and/or attachment for rotatably supporting a cutter is made from a polymer of polyimide resin and graphite material and is designed to have a polygon configured bore where there are two point contact of the mating surfaces of the bore walls and cutter's shaft and preferably the bore is square shaped in cross section. This bearing results in a decrease in the envelope size of the support tube and hence, the overall diameter of the surgical instrument at the distal end enhances the line of vision of the cutter to the surgeon when the surgeon is performing surgical procedures. The entrance ends of the intermediate bearings are countersunk to define a ramp to ease the egress of the tool bit shaft for entering the tube of the drill motor or drill attachment during the assembly thereof.

6 Claims, 4 Drawing Sheets

BEARINGS FOR SURGICAL INSTRUMENTS

TECHNICAL FIELD

This invention relates to bearings for rotary support of rotating cutting tools and more particularly for bearings used to support the cutting tool in surgical drill motors and/or attachments therefor.

CROSS REFERENCES

The following patent applications, contemporaneously filed with this patent application and assigned to the same assignee relate to the subject matter of this patent application and are incorporated herein by reference. They include the patent application Ser. No. 09/962,461 entitled "Miniature Cutter Shaft Configuration" filed by Eddy H. Del Rio, Douglas Perry, Jose M. Lamanna, and Thomas D. Anspach and the patent application Ser. No. 09/962,957 entitled "Miniature Clutch for High Speed Surgical Drills" filed by Eddy H. Del Rio, Douglas A. Perry, Jose M. Lamanna and Thomas D. Anspach.

BACKGROUND OF THE INVENTION

As one skilled in the medical technological field appreciates, the surgeon that uses surgical drills for performing surgery on a patient and particularly, in the neurological arena, requires that the instruments have a satisfactory "feel" and "visual efficacy". In other words, the surgeon needs to feel not only confident in the quality and efficacy of the surgical instrument being used, that the tool has structural integrity and reliance, he would also like to be capable of seeing what is happening where the cutting is taking place. Obviously, ball bearings are typically used for high speed rotary types of instruments because they afford low friction and satisfactory rotary support. However, because the ball bearings require inner and outer races in addition to the balls, the envelope to house these bearings is typically large. For example, the diameter of the working end (distal end) of surgical drills with or without adapters are at a minimum equal to 5–7 millimeters. Although the cutting tool projects a small axial distance from the end of the drill/adapter, which is dictated by structural integrity, bending loads, etc., this diameter of the support mechanism at the distal end of the instrument impedes the line of sight of the surgeon while working within the patient's cavity. This invention constitutes an improvement over the mechanism disclosed in U.S. Pat. No. 5,405,348 granted on Apr. 11, 1995 to William E. Anspach, Jr. and Eddy H. Del Rio, a joint inventor of this patent application, entitled "Surgical Cutting Instrument". In the positive bearing in the support tube for supporting the shaft of the cutter, the support tube is configured into a triangular shape and carries three circumferentially disposed lands made from a low coefficient of friction and high density material. It is apparent merely from a visual inspection of this bearing, that it is more complicated to fabricate this type of bearing construction, since the bearing plates require retaining means to hold them into the desired position. Whereas, the journal bearing of this invention, merely requires insertion into the tube without anything further. Also, the bearing disclosed in the U.S. Pat. No. 5,405,348 patent, supra, requires lubrication and cooling for the bearing or it would otherwise fail instantly or substantially instantly. The inventive bearing described hereinbelow does not require lubrication and/or cooling.

We have found that by judiciously configuring the bearing and making the bearing out of a given polyimide material, we can significantly reduce the bearing size without sacrificing speed, integrity and reliability, with a consequential reduction in the size of the envelope where the bearing are housed and likewise, obtain a consequential reduction in the outer diameter of the instrument at the distal end. Hence, the overall diameter of the distal end is made sufficiently small to overcome the visual problems evidenced in heretofore known surgical instruments of this type. We have found that we can reduce the outer diameter by 50% or more.

In addition, since the cutting tool is made to be removably inserted into the motor or adapter, it is necessary to assure that the shaft of the tool bit is inserted through the bearings with ease and without being cumbersome to install. To this end, the intermediate bearings, i.e. the bearings out of sight of the operator are judiciously countersunk to define a ramp that serves to guide the shaft into and/or through the bearing.

SUMMARY OF THE INVENTION

An object of this invention is to provide an improved bearing for a surgical instrument that reduces the overall diameter size of the surgical instrument and enhances the line of sight for the surgeon.

A feature of this invention is to configure the inner diameter of the bearing in a substantially square configuration in cross section and to make the bearing out of a polyimide resin material. The size of the bearing and shaft is predicated on there being a point contact during the operating envelope of the surgical drill or the attachment. Other cross sectional configurations, other than circular, can be utilized so long as these configurations have the two point contact during the rotational envelope of the drill or attachment.

A still further feature is to use a polyimide resin and carbon/graphite material for the bearing.

A still further feature is to make the bearing from VESPEL (a product of the Dupont Company) SP-22 or SP-21 material.

Another feature of the invention is to contour the inlet side of the bearing to guide the shank of the tool bit into and through the bearing.

The foregoing and other features of the present invention will become more apparent from the following description and accompanying drawings.

These figures merely serve to further clarify and illustrate the present invention and are not intended to limit the scope thereof.

DETAILED DESCRIPTION OF THE INVENTION

While the invention being described herein discloses in the preferred embodiment the inventive bearings being used in an angled adapter referred to herein as a Micro Dissection Attachment (MDA) it is to be understood that the invention has utility in any other rotary instrument where bearings are required to support a rotating shaft. This particular instrument is particularly adapted for surgical procedures for performing delicate operation like transoral, transphernoidal and similar restricted access approaches.

Figure 1:
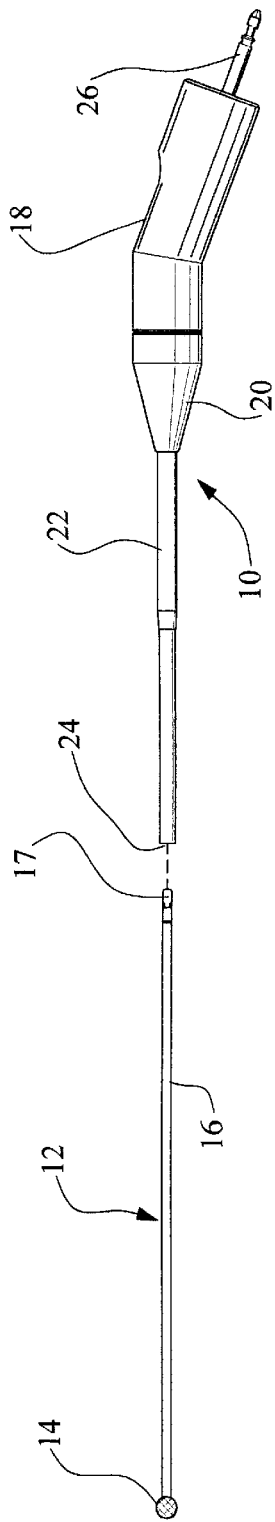
FIG. 1 is a perspective view of an angled adapter utilizing this invention for use with a surgical drill motor for supporting a tool bit.

To best understand this invention reference is made to FIG. 1 which discloses an MDA generally illustrated by reference numeral 10 which is dimensioned with a minimum diameter of 3 mm at the distal end, being 15 cm long and bent at a 20 degree (°) angle, for example, that rotatably supports a tool bit 12 (only partially shown) having a cutting end 14 at the distal end, an elongated shaft 16 and a clutch portion (not shown) at the proximal end. The body of the MDA includes the angled housing 18, the nose cone member 20 extending from the fore end of the angled housing 18, an elongated tube assembly 22, that may be stepped toward the distal end 24 and the drive shaft 26 with its clutch shaped end that fits into the drill motor (not shown). The drill motor may be any of the surgical motors manufactured by the assignee of the present invention known in the industry as eMax™ and microMax™ or any other drill motor. (A suitable motor is commercially available from Anspach Companies, Palm Beach Gardens, Fla). For additional information regarding surgical drills of the type being described herein reference should be made to U.S. Pat. Nos. 5,405,348, 5,494,359 and 5,601,560, which are incorporated herein by reference.

Figure 3:
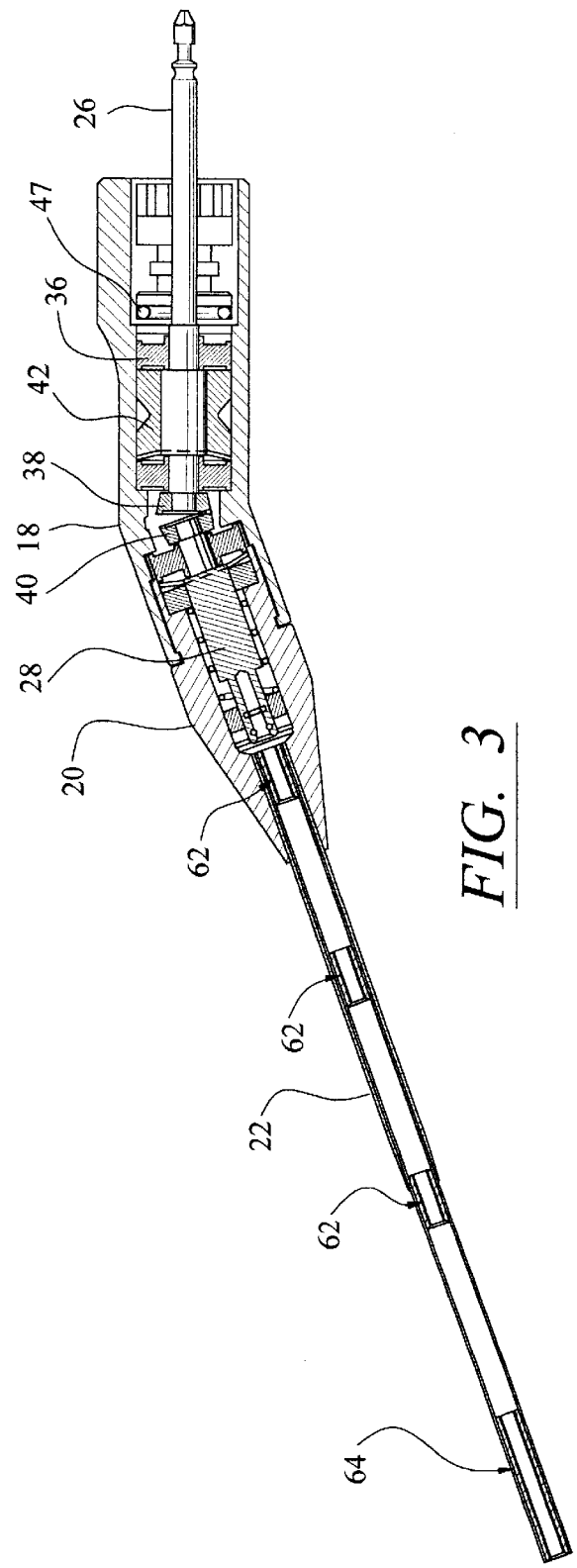
FIG. 3 is a sectional view of the adapter of FIG. 1.
Figure 2:
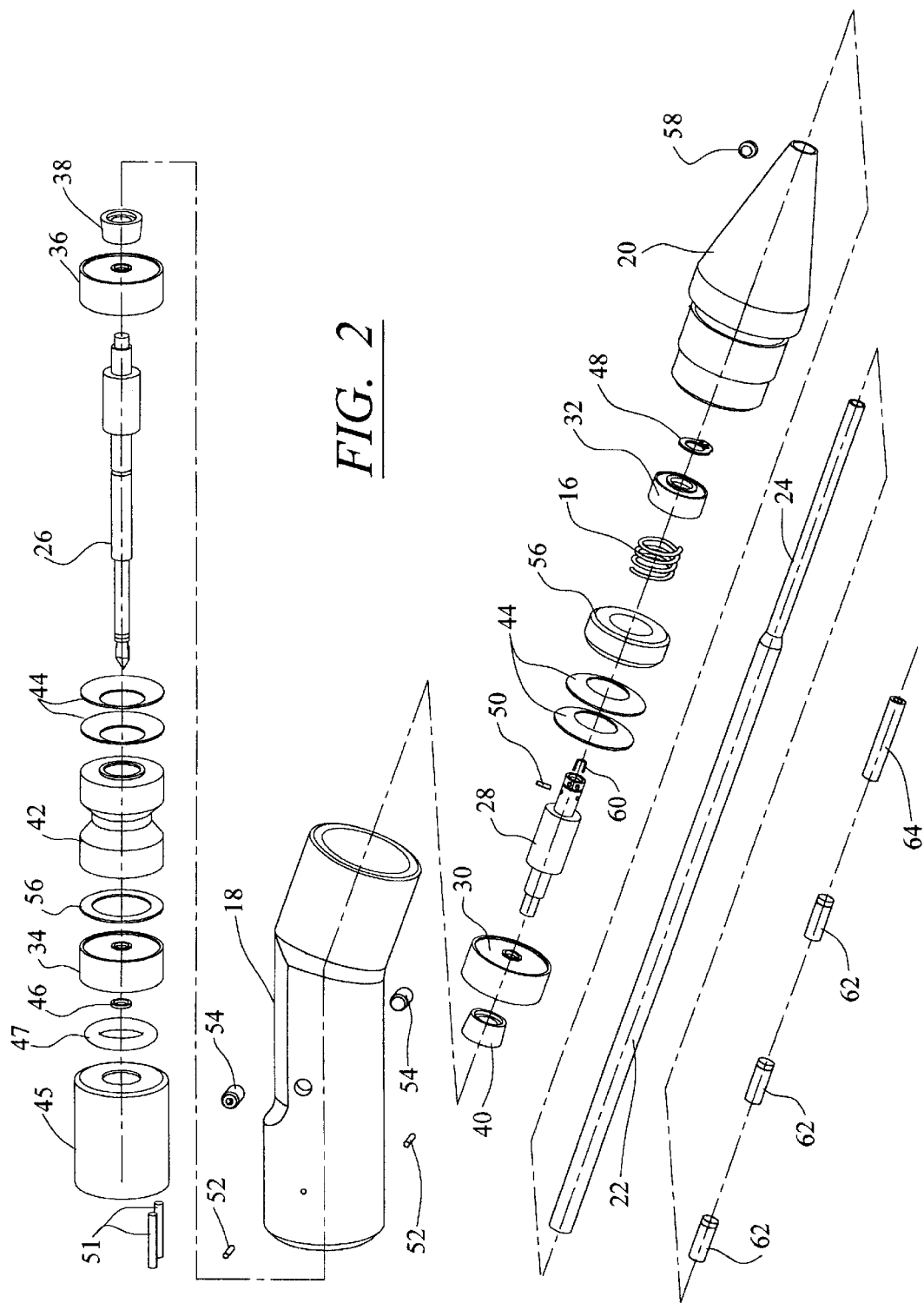
FIG. 2 is an exploded view of the adapter depicted in FIG. 1.
Figure 4:
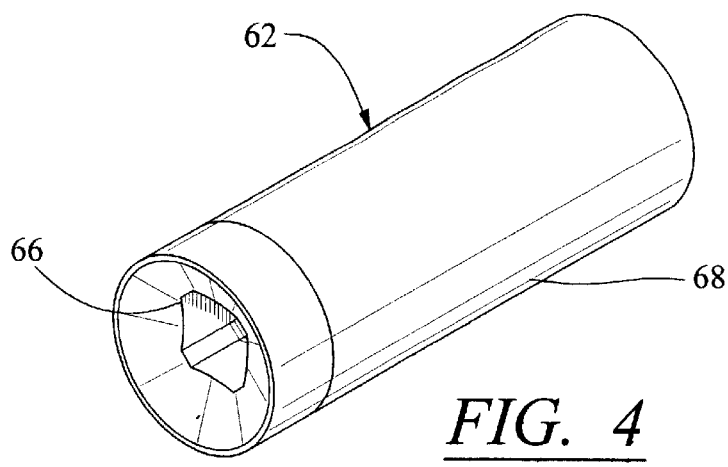
FIG. 4 is a perspective view of a intermediate bearing of this invention.
Figure 5:
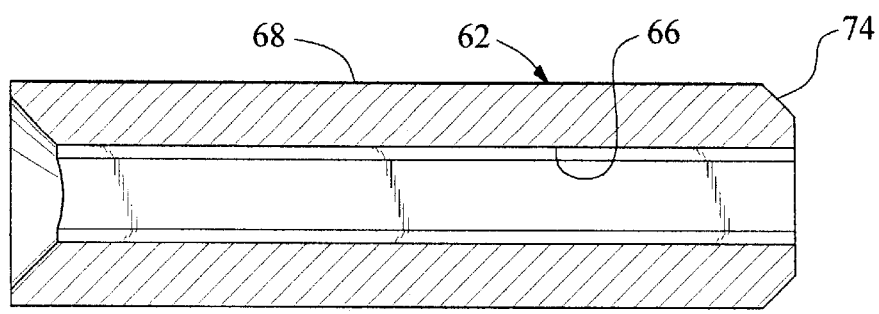
FIG. 5 is a sectional view of the bearing depicted in FIG. 4.
Figure 5A:
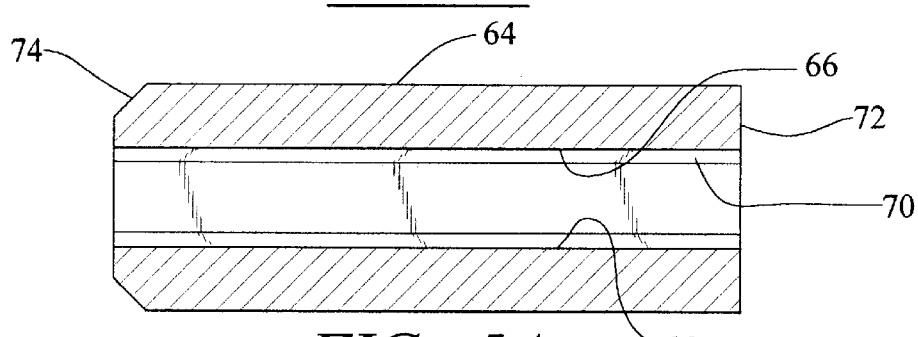
FIG. 5A is a sectional view of an intermediate bearing of the invention.
Figure 6:
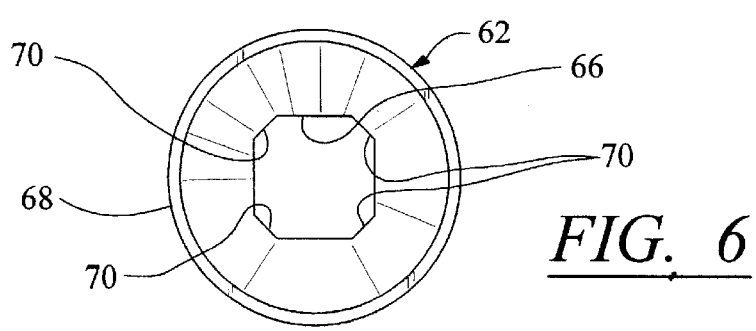
FIG. 6 is a front end view of the bearing depicted in FIG. 5.

Next referring to FIGS. 2 and 3 which illustrate the details of the MDA and the bearings of this invention which consists of a spindle 28 that is suitably rotatably supported by commercially available and suitable ball bearings 30 and 32. As is apparent from FIG. 3 the drive shaft 26 is also suitably rotatably supported in the angled housing 18 by commercially available and suitable ball bearings 34 and 36. As mentioned in the above paragraphs the drive shaft is suitably coupled to the drill motor (not shown) and driven thereby. The drill motor may use any medium for developing rotational movement and in this instance these motors are air driven. As noted, the spindle 28 is angled relative to the drive shaft 26 requiring beveled gears to change the relative angle. Suitable bevel gears 38 and 40 mounted on drive shaft 26 and spindle 28, respectively, provide this function. The thrust is absorbed by the thrust bearing 36 and the bearings are pre-loaded by the wave washer 57 and coil spring 16. The bushing 45 mounted in the aft end of the angle housing 18 is designed to accommodate the fitting connection in the drill motor which includes coupling mechanism that removably affix the MDA thereto. Suitable snap rings 46, 48, anti-rotation pins 51, spring pins 52 and set screws 54 are utilized to lock the respective components in the housing and together with the thrust washers 56 and wave washer 57 assure that the spindle is snugly fitted into the angled housing 18 and rotates efficaciously and attains long life. An seal 47 may be mounted in the angled housing at the drill attachment end to prevent contaminants from migrating internally and a suitable seal may be a commercially available "O" seal made from an elastomeric material. As mentioned in the above paragraphs, the drive motor and the MDA are merely used herein to describe the preferred embodiment. The invention is the utilization of the inventive bearings that are inserted into the tube assembly 22 which is affixed to the nose cone 20 by the set screw 58 and is held in a non-rotational position.

The end of the shaft 16 of the drill bit 12 is configured to fit into a complementary configured retaining bore 58 formed internally of one end of the spindle 28 and together with the latch spring 60 and lock pin 50, locks the drill bit into place so that it rotates therewith. While these configurations are novel and unique in this particular embodiment and is disclosed in a patent application filed contemporaneously herewith and entitled "Miniature Coupler for a High Speed Drill" and is commonly assigned to the same assignee as this patent application Ser. No. 09/962,957, it should be understood that any other coupling mechanism can utilized without departing from the scope of this invention. Also the proximate end of the shaft of the cutting tool bit is complementary contoured and together with the coupler in the adapter or motor serve to couple the tool bit to the adapter or motor to rotate therewith. While the coupler mechanism is novel and described in a copending patent application entitled "Drill Bit Surgical Cutter" and commonly assigned to the same assignee Ser. No. 09/962,461, U.S. Pat. No. 6,607,533 as this patent application, it should be understood that any well known coupler can be utilized without departing from the scope of this invention.

In this particular embodiment, four (4) similar bearings are utilized with the internal bearings generally indicated by reference numeral 62 and the distal end bearing generally indicated by reference numeral 64. For the sake of convenience and simplicity, only one of the internal bearings 62 and the distal end bearing 64 will be described.

In accordance with this invention all the bearings are made from a synthetic material and preferably polyimide resin and carbon or graphite. The best results have been obtained when the polyimide resin by volume equaled 60 percent (%) of the total volume and the carbon/graphite equaled 40% of the total volume. The material is obtained commercially and is made by Dupont under the trademark of "VESPEL". "VESPEL" SP-22 and SP-21 have been used and worked satisfactory. The intermediate bearing 62 are formed similar to a journal bearing with the inner straight through bore 66 formed in the cylindrical housing 68 is configured in a square shape in cross section and the corners 70 extending straight through the bore are beveled. The beveled portions are only incorporated to add material to the bearing, and hence, increase its structural integrity. The inlet portion, i.e. the portion facing the distal end 24 of the tube 22, is beveled in a countersunk manner so as to form a ramp to assist the end of the shaft 16 of the tool bit 12 to enter and pass into and/or through the bearing. The end portion 72 of bearing 64 at the distal end is squared off and hence, not countersunk. The proximal ends of the bearings 62 and 64 may be beveled in order to ease the assembly of the bearings when inserted into the tube 22. Obviously, the bearing outer diameter is selected to assure a tight fit with the interior surface of the tube 22.

The surgical instrument built in accordance with this invention has been tested and operated satisfactory for cutting bone and with a motor that rotates the drill bit over 80,000 RPM and without the use of lubricant for the inventive bearings or providing cooling therefor.

Figure 7:
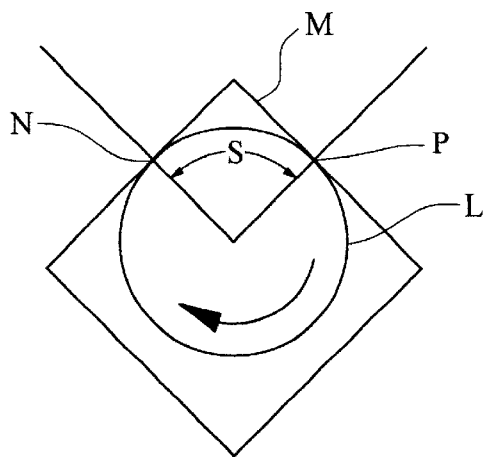
FIG. 7 is an enlarged and exaggerated schematic illustration of the square configuration and the two point contact of the inventive bearing.
Figure 8:
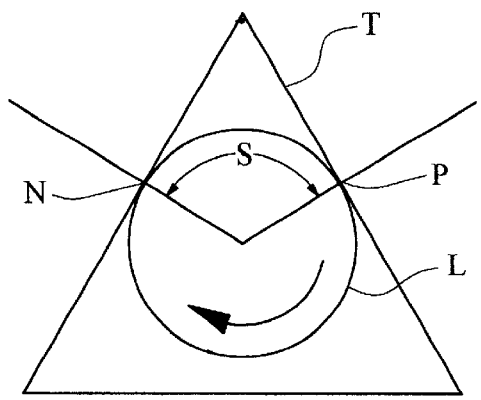
FIG. 8 is an enlarged and exaggerated schematic which exemplifies another configuration of the inventive bearing with a two point contact.
Figure 9:
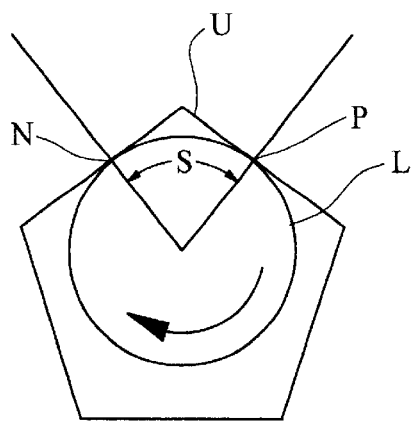
FIG. 9 is an enlarged and exaggerated schematic exemplifying another configuration of the inventive bearing with a two point contact.
Figure 10:
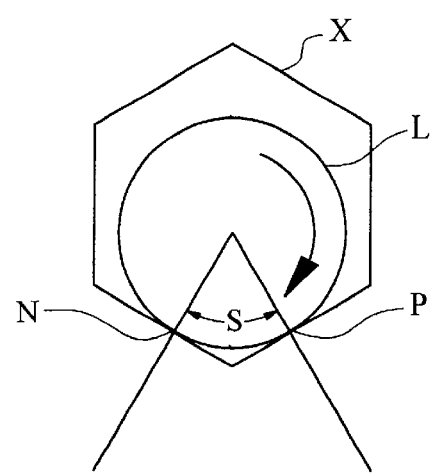
FIG. 10 is an enlarged and exaggerated schematic exemplifying another configuration of the inventive bearing with a two point contact.

While the broached square bore configuration as described in the immediately above paragraphs is the preferred embodiment, it should be understood that other polygon configurations can be employed. However, in accordance with this invention, the shaft when rotating in the bearing bears on only two surfaces. Hence, the dimensions of the shaft and the bore are predicated on this essential aspect. This feature is illustrated in FIGS. 7–10 which shows the shaft and bearing in schematic where the shaft is illustrated by reference letter L and the bore in the bearing is illustrated by reference numeral M. FIG. 7 is illustrative of the square brooch and it will be appreciated that the points of contact between the bearing and the shaft are N and P with the inclusive angle S emanating from the center of the shaft L is substantially equal to 90°. (All reference letters used in these Figs. depict the same features). FIG. 8 illustrates the bore T configured in a triangular shape in cross section and the inclusive angle S between the contact points N and P is substantially equal to 120°. FIG. 9 illustrates the cross sectional configuration of bore U is a pentagon with the inclusive angle S between contact points substantially equal to 100°. In FIG. 19 the cross section of the bore X configuration is a hexagon with the inclusive angle S between the contact points N and P substantially equal to 50°. Obviously, so long as there are only two contact points between the shaft and bore surface, almost any polygon configuration can be utilized without departing from the scope of this invention.

Although this invention has been shown and described with respect to detailed embodiments thereof, it will be appreciated and understood by those skilled in the art that various changes in form and detail thereof may be made without departing from the spirit and scope of the claimed invention.

We claim:

1. In combination, an attachment for a high speed surgical drill motor having a rotatable spindle rotated by the high speed surgical drill motor, a cutter adapted to be inserted into a cavity formed in said rotatable spindle and including means for locking said cutter into said rotatable spindle to be rotated therewith, said attachment including a tubular member extending axially from one end of said attachment, said tubular member including at least two axially spaced bearings, each of said bearings including a cylindrical housing having an outer surface rigidly mounted in said tubular member and a square brooch defining a straight through bore forming the bearing surface of said bearing to rotatably support said cutter, said cutter being removable and having an elongated shaft slidably mounted in said straight through bore defining the mating surface with said bearing surface, the area of the cross section of said straight through bore being selected so that said high speed rotating shaft bears at point contact against two adjacent side wall surfaces of said four side wall surfaces said bearing made from VESPEL SP-22 or SP21 material.

2. In combination, an attachment for a high speed surgical drill motor having a rotatable spindle rotated by the high speed surgical drill motor, a cutter adapted to be inserted into a cavity formed in said rotatable spindle and including means for locking said cutter into said rotatable spindle to be rotated therewith, said attachment including a tubular member extending axially from one end of said attachment, said tubular member including at least two axially spaced bearings, each of said bearings including a cylindrical housing having an outer surface rigidly mounted in said tubular member and a square brooch forming the bearing surface of said bearing to rotatably support said cutter, said cutter having an elongated shaft defining the mating surface with said bearing surface, said square brooch includes four side surfaces defining four corners and each of said corners being faired to define an extended surface to increase the total amount of material forming said bearing so as to increase the structural integrity of the bearings, and said bearings made from a group of polymers consisting essentially of polyimide resin and graphite.

3. In combination, an attachment for a high speed surgical drill motor as claimed in claim 2 wherein the volume of the polyimide is substantially equal to between 60%–85% of the total volume and the volume of graphite is substantially equal to between 40%–15% of the total volume of the material.

4. In combination, an attachment for a high speed surgical drill motor as claimed in claim 2 wherein the volume of the polyimide is substantially equal to 60% of the total volume and the volume of graphite is substantially equal to 40% of the total volume of the material.

5. In combination, an attachment for a high speed surgical drill motor as claimed in claim 2 wherein one of said bearings includes a fore end and an aft end, said fore end being countersunk to define a ramp for guiding said high speed rotating shaft into said bearing when installing said high speed rotating shaft and said one of said bearings being mounted intermediate the ends of said tubular member.

6. An attachment for a high speed surgical drill motor having a rotatable spindle rotated approximately 80,000 revolutions per minute by the high speed surgical drill motor, a cutter adapted to be inserted into a cavity formed in said rotatable spindle and including means for locking said cutter into said rotatable spindle to be rotated therewith, said attachment including a tubular member extending axially from one end of said attachment, said tubular member including at least two axially spaced bearings, each of said bearings including a cylindrical body having an outer surface rigidly mounted in said tubular member and a square brooch defining a straight through bore defining four side wall surfaces forming the bearing surface of said bearing to rotatably support said cutter, said cutter being removable and having an elongated shaft slidably mounted in said straight through bore defining the mating surface with said bearing surface, the area of the cross section of said straight through bore being selected so that said high speed rotating shaft bears at point contact against two adjacent side wall surfaces of said four side wall surfaces, and said bearing made from a plastic and graphite composite material.

\* \* \* \* \*